US005417713A

United States Patent [19]
Cohen

[11] Patent Number: 5,417,713

[45] Date of Patent: May 23, 1995

[54] TRANSESOPHAGEAL DEFIBRILLATING SYSTEM

[75] Inventor: Todd J. Cohen, Port Washington, N.Y.

[73] Assignee: Leonard Bloom, Towson, Md. ; a part interest

[21] Appl. No.: 15,544

[22] Filed: Feb. 9, 1993

[51] Int. Cl.[6] .............................................. A61N 1/39

[52] U.S. Cl. .......................................... 607/4; 607/124

[58] Field of Search ...................... 607/124, 4, 5, 119, 607/122, 124, 129, 133, 142

[56] References Cited

U.S. PATENT DOCUMENTS

| | | | |
|---|---|---|---|
| 4,603,705 | 8/1986 | Speicher et al. | 607/122 |
| 4,640,298 | 2/1987 | Pless et al. | 607/124 |
| 4,919,147 | 4/1990 | Reinhardt et al. | 607/124 |
| 4,960,133 | 10/1990 | Hewson | 607/124 |
| 5,003,991 | 4/1991 | Takamaya et al. | 607/116 |
| 5,036,848 | 8/1991 | Hewson | 128/642 |
| 5,178,149 | 1/1993 | Imburgia et al. | 607/124 |
| 5,179,952 | 1/1993 | Buinevicius et al. | 128/642 |
| 5,191,885 | 3/1993 | Bilof et al. | 607/124 |
| 5,265,623 | 11/1993 | Kroll et al. | 607/122 |

*Primary Examiner*—William E. Kamm

*Assistant Examiner*—Marianne Parker

*Attorney, Agent, or Firm*—Leonard Bloom

[57] ABSTRACT

A transesophageal defibrillating system includes a large area anterior patch electrode and a large area posterior patch electrode, as in some conventional exterior defibrillating systems. An esophageal probe has a pair of ring electrodes, one of which is carried at or near its distal end. The system is operatively arranged to supply defibrillation pulses between the large anterior patch electrode and either the distal electrode (carried by the probe) or the large posterior electrode, depending on which one of the latter two electrodes is connected or coupled by the clinician or paramedic to the defibrillating pulse source. The system includes a source of pacing pulses which may be supplied to the patient via the anterior patch electrode and at least one of the electrodes carried by the esophageal probe. The distal electrode is believed to be the more effective electrode to use for this purpose. The system also preferably provides for sensing, displaying and recording ECG signals, the two electrodes carried by the probe supplying input representing electrical activity of the heart for display and/or recording.

36 Claims, 9 Drawing Sheets

TRANSESOPHAGEAL DEFIBRILLATING SYSTEM

BACKGROUND OF THE INVENTION

1. Field of the Invention

The present invention relates generally to a system for defibrillating a heart. More particularly, the invention relates to a system for defibrillating a heart using a transesophageal path. The invention also concerns such a system which, in the alternative, allows use of a transthoracic path for the defibrillating energy. The invention may provide for pacing the heart and/or ECG monitoring.

2. Prior Art

Sudden cardiac death from ventricular fibrillation is a leading cause of mortality. The most important factor in determining patient survival is early defibrillation. However, a significant percentage of patients with cardiac arrest present with refractory ventricular fibrillation. These patients may not respond to standard cardiopulmonary resuscitation, transthoracic shocks, or drug therapy. The clinician, therefore, must decide whether to continue or terminate the resuscitative effort.

The most common mechanisms for high defibrillation thresholds include elevated transthoracic resistance due to obesity or chronic obstructive pulmonary disease, prolonged duration of ventricular fibrillation, presence of ischemia or anaerobic metabolism, and superimposed drug therapy.

The success of a transthoracic shock is partially dependent upon the distance of the energy-applying electrodes from the heart, which is one determinate of transthoracic impedance. A more effective method of defibrillation would involve placement of defibrillator probes either into or in close proximity to the myocardium. Recently, intracardiac transcatheter defibrillation has provided a means of defibrillation for patients with refractory ventricular fibrillation induced in the electrophysiology laboratory. This technique is performed by defibrillating between a distal right ventricular pacing electrode and a posterior skin patch. The impedance between these two electrodes is less than the impedance between two electrodes located in standard positions on the thorax. This method, however, is performed most expeditiously if a temporary pacing lead is already present in the right ventricle.

In the past, transesophageal techniques have been employed primarily for atrial pacing and cardioversion of atrial arrhythmias. A braided copper esophageal electrode (15 cm in length; 9 mm in diameter) has been tested in conjunction with a maliable lead precordial electrode and was capable of terminating ventricular fibrillation in canines using high energy defibrillation, as reported in Whipple G. H. et al., "Transesophageal Ventricular Defibrillation" (abstr.), *Clin Res* 1956; 4:105. The effect of cardioverting using a Levine tube wound with copper wire is known and has been reported in McNally E. M. et al., "Elective Countershock In Unanesthetized Patients With Use Of An Esophageal Electrode", *Circulation* 1966; 33:124–127. This was accomplished by delivering direct current energy between the esophageal electrode to a precordial patch in 13 patients with atrial fibrillation. More recently, it has become known that a French hexapolar esophageal probe in canines was used to successfully terminate ventricular tachycardia and fibrillation; see Yunchang C. et al., "Transesophageal Low-Energy Cardioversion In An Animal Model of Life-Threatening Tachyarrhythmias", *Circulation* 1989; 80:1354–1359. These arrhythmias were terminated immediately and thus did not assess the potential for rescue defibrillation of refractory ventricular fibrillation. However it is unlikely that these prior art techniques would be effective in cardiac arrest patients in light of the small electrode surface area as well as the low energies employed.

It has been recognized that when a person's heart is beating at a slow or an irregular rate, or after defibrillation, the heart should be stabilized to beat at a particular rate. An electronic pacing method and apparatus is known from U.S. Pat. No. 4,574,807 which can achieve such pacing without surgery using a flexible tube or rod having a series of circumferential electrically conductive rings spaced a few centimeters apart and electrically connected together which may be inserted down the esophagus so as to place the rings in the lower portion thereof. A second electrode, which may be a conventional adhesively attached ECG electrode, is attached to the sternum. An electrical pacing pulse of short duration and low power is passed between the electrodes. The pulses stimulate the heart muscles and make the heart beat at a preset rate. The tube or rod carrying the electrically-connected-together rings may be small enough to pass through an esophageal gastric tube or similar device. No provision is made for supplying defibrillating energy.

A somewhat more complex system for pacing the heart from the interior of the esophagus, is disclosed in U.S. Pat. No. 4,640,298 which discloses a probe constructed on the basis of a finding that the distance from the transition between the stomach and the esophagus to the transition between the left atrium and the left ventricle is substantially the same in adults. The electrode probe has a maximum of two stimulation zones (one for atrium and ventricle, respectively) which, when fitted on expansible parts of the probe, allows heart pacing to be performed with simple equipment without expert assistance, when the distance between a means for fixing the axial position of the probe in the esophagus and the stimulation zones are determined in accordance with the finding. Good stimulation of the heart and reduction in the required pacing voltages are achieved. No provision is made for supplying defibrillating energy.

A non-invasive cardiac device is disclosed in U.S. Pat. No. 4,706,688 which can be inserted through the esophagus and into the gastroesophageal junction region. Once in place, a selected portion of the device is urged adjacent the cardiac region. The device includes an elongated conduit having a series of spaced-apart ring electrodes for sensing or recording electrical signals. A first inflatable cuff is provided for positioning the device adjacent the gastroesophageal region is located adjacent a first end of the device. The device further includes a second inflatable cuff for positioning the device in the esophagus such that at least some of the ring electrodes carried by the conduit are urged adjacent the cardiac region. The spaced-apart electrodes are used in pairs to pass electrical signals to the heart for atrial/ventricular pacing and to receive electrical signals from the heart for electrogram analysis. It is proposed to supply low current defibrillating energy to the heart, apparently via a pair of the ring electrodes carried by the conduit. Neither an anterior patch nor a posterior patch is provided for any purpose.

A method and apparatus are disclosed in U.S. Pat. No. 4,735,206 to provide defibrillating energy to a heart using a small internal esophageal electrode and an external small chest electrode. The two small intimately located electrodes, one in the lower esophagus where it is intimate to the posterior section of the heart and the other small electrode on the chest over the sternum where it is close to the anterior portion of the heart, provide an electrical path between the two electrodes. An electrical pulse having a peak of approximately 150 volts is delivered. During this period, gentle repolarizing of the heart takes place. When the heart is repolarized, the heart cells become neutral. They are vulnerable to a stimulus. The defibrillation pulse may be immediately followed by a stimulus in the form of pacing pulses that are at the rate of approximately 70 to 100 pulses per minute and of a magnitude of approximately 75 to 150 milliamps. The switch from one mode to the other is made without changing the location of the electrodes. No provision is made for providing a plurality of electrically separated electrodes within the esophagus nor a large area patch on the chest.

A method and apparatus for achieving atrial defibrillation or ventricular defibrillation using a small single, internal esophageal electrode and a single moveable small external chest electrode is disclosed in U.S. Pat. No. 5,052,390. Atrial defibrillation is attempted using the internal esophageal electrode and with the small external chest electrode placed approximately on a line between the two nipples and part way between the sternum and the left nipple. This provides a good path for the defibrillating pulse so that defibrillation is said to be accomplished with very low power of 30 to 70 joules (average 50 joules) compared to what is normally used, namely, 100 to 360 joules. Ventricular defibrillation is said to be possible using the small internal esophageal electrode and an external chest electrode placed approximately over the apex of the left ventricle. This provides a good path for the defibrillating pulse so that the power needed, it is said, may be of the same magnitude as that used for atrial defibrillation for the purpose of ventricular defibrillation. No provision is made for providing a plurality of electrodes within the esophagus nor a large area patch on the chest.

SUMMARY OF THE INVENTION

An object of the present invention is to provide a defibrillating system which includes an esophageal electrode and a large area anterior patch electrode or the like particularly useful in treating patients with refractory ventricular fibrillation during cardiac arrest.

Another object of the present invention is to provide a defibrillating system which includes a large area anterior patch electrode or the like, an esophageal electrode and a large area posterior patch electrode or the like, the esophageal electrode replacing the posterior patch electrode during patient rescue attempts.

A further object of the present invention is to provide a defibrillating system of the type mentioned in the foregoing objects which has pacing capabilities as well.

An additional object of the present invention is to provide a defibrillating system of the type mentioned in the foregoing objects which provides for ECG monitoring, using electrodes carried by an esophageal probe which is part of the system.

Yet another object of the present invention is to provide an esophageal probe especially useful in defibrillating systems, pacing systems and/or ECG monitoring systems.

The above-noted objects, as well as others which become apparent from the specification and drawings of the present application, are achieved in accordance with the present invention, by providing a transesophageal defibrillating system which includes a large area anterior patch electrode and a large area posterior patch electrode, as in some conventional exterior defibrillating systems. Circuitry is provided to supply alternatively defibrillating pulses between either the posterior patch electrode and the anterior patch electrode or the anterior patch electrode and one of two electronically separated, spaced-apart electrodes carried by an esophageal probe, one of the electrodes being at or near the distal end of the probe. The second electrode which is also carried by the probe can be viewed as a proximal electrode. The system supplies defibrillation pulses between the large anterior patch electrode and either the distal electrode (carried by the probe) or the large posterior patch electrode, depending on which one of the latter two electrodes is connected or coupled by the clinician or paramedic to the defibrillating pulse source. The system includes a source of pacing pulses which may be supplied to the patient via the anterior patch electrode and at least one of the electrodes carried by the esophageal probe. The distal electrode is believed to be the more effective electrode to use for pacing. The system also preferably provides for sensing, displaying and recording ECG signals, the two electrodes carried by the probe supplying input representing electrical activity of the heart to a display and/or recorder.

The novel features that are considered characteristic of the invention are set forth with particularity in the appended claims. The invention itself, however, both as to its organization and operation, together with other objects and advantages thereof, is to be understood from the following description of illustrative embodiments, when read in conjunction with the accompanying drawings, wherein like reference numerals refer to like components.

DETAILED DESCRIPTION OF PREFERRED EMBODIMENTS

Figures 1, 1A:
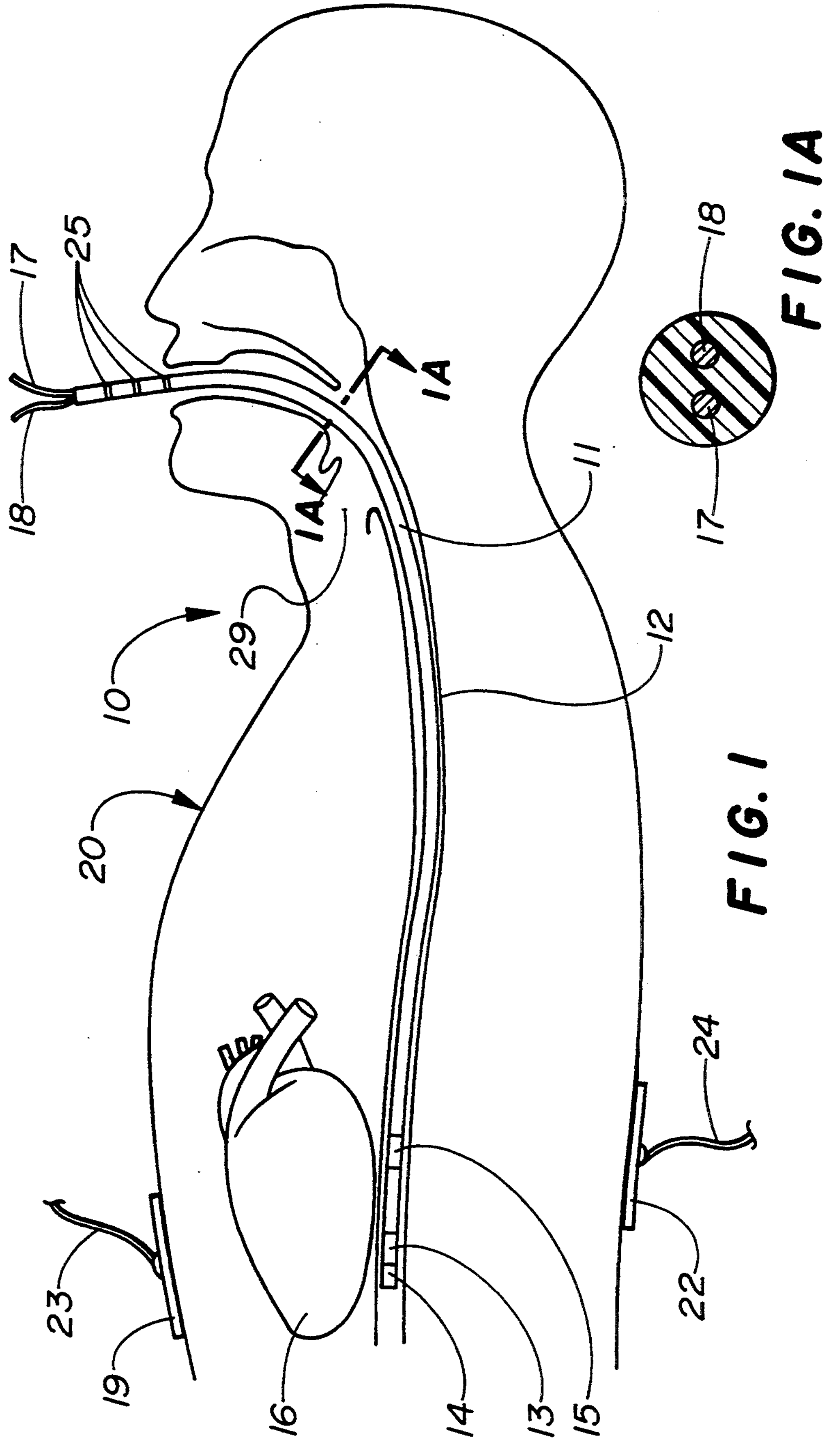
FIG. 1 is a pictorial view of a first embodiment of an esophageal probe and electrode arrangement, in accordance with the present invention, which is suitable for practicing the invention in its system aspect, a patient being shown in phantom.
FIG. 1A is a cross-sectional view of the probe shown in FIG. 1, the section being taken along section line 1A—1A.

As illustrated in FIGS. 1 and 1A, an exemplary first embodiment of the esophageal probe and electrode arrangement is shown pictorially as used with a patient (subject) 10, shown in phantom. An elongated, flexible probe 11, shown positioned within the esophagus 12 of the subject 10 is provided. The probe 11 is made of electrically insulative material, such as a plastic, and is cylindrical in cross section. The probe 11, in some realized embodiments, is approximately one-half an inch in diameter. The probe 11 carries fixedly on its outer surface a first, generally cylindrical, metal electrode 13 positioned near its distal end 14. In some cases, the electrode 13 could be positioned adjacent the distal end 14 of the probe 11 or be fixed to the distal end. The first electrode 13 is approximately one and one-eighth inches in length, providing appropriate surface area to carry and distributed relatively high defibrillating currents. A second, generally cylindrical, metal electrode 15 fixedly carried by the probe 11 is positioned, in realized embodiments, approximately two and five-eighths inches from the proximal end of the first electrode 13. When in its operative position, the electrode 15 is positioned close to the heart 16 of the subject 10, in the vicinity of its atrial area. A first electrically conductive, insulated lead 17 and a second, electrically conductive, insulated lead 18 extend respectively from beyond the proximal end of the flexible probe 11, as illustrated in FIG. 1A, within the probe to the respective metal electrodes 13 and 15. One purpose of the leads 17 and 18 is to provide an electrical path from the respective electrodes 13 and 15 so that, in a monitoring mode, bipolar ECG signals can be supplied from these electrodes. A second purpose of the leads 17 and 18 is to provide respective possible pacing inputs to the heart 16 of the subject via the respective metal electrodes 13 and 15, the electrode 13 being preferred because it is positioned nearer the ventricular area of the heart 16.

As positioned in its operative position within the esophagus 12 of the subject 10, the distally positioned electrode 13, when in its operative position, is near the heart 16 of the subject, in very close vicinity to the ventricular area of the heart. A first conventional, large area, metallic patch electrode 19 is positioned over the anterior of the thorax 20 of the subject 10 in the vicinity of the sternum. The electrode 19 may be in the form of a rectangular mesh approximately four inches long and two inches wide provided with a foam rubber overlay which is rectangular in shape and extends peripherally beyond the edges of the electrode to define an area having an adhesive thereon for holding the electrode adjacent to the skin of the subject 10.

As illustrated, a second conventional, large area, metallic patch electrode 22 is shown positioned over a large area of the posterior of the thorax 20 of the subject 10. The second patch electrode 22 may be of the same size and shape as the electrode 19. It is to be appreciated that the second patch electrode 22 is positioned in the position shown whenever a clinician or paramedic elects to effect defibrillation via the transthoracic route. In this case defibrillating pulse(s) is (are) applied between the first patch electrode 19 and the second patch electrode 22, the anterior patch electrode 19 acting as the negative (cathode) electrode while the posterior patch electrode 22 acts as the positive (anode) electrode. A third, electrically conductive, insulated lead 23 is provided as an electrical connection to the anterior patch electrode 19. A fourth, electrically conductive, insulated lead 24 provides an electrical connection to the posterior patch electrode 22.

Were the clinician or paramedic to determine that rescue defibrillation should be attempted via the transesophageal route, the patch electrode 22 would be removed from the subject or disconnected from the defibrillation source (not shown) and the defibrillating pulse or pulses applied between the distal, first electrode 13 and the anterior patch electrode 19. As in the transthoracic route, the patch electrode 19 acts as the negative (cathode) electrode; the distally positioned electrode 13 carried by the probe 11, in this case, acts as the positive (anode) electrode.

Figure 5:
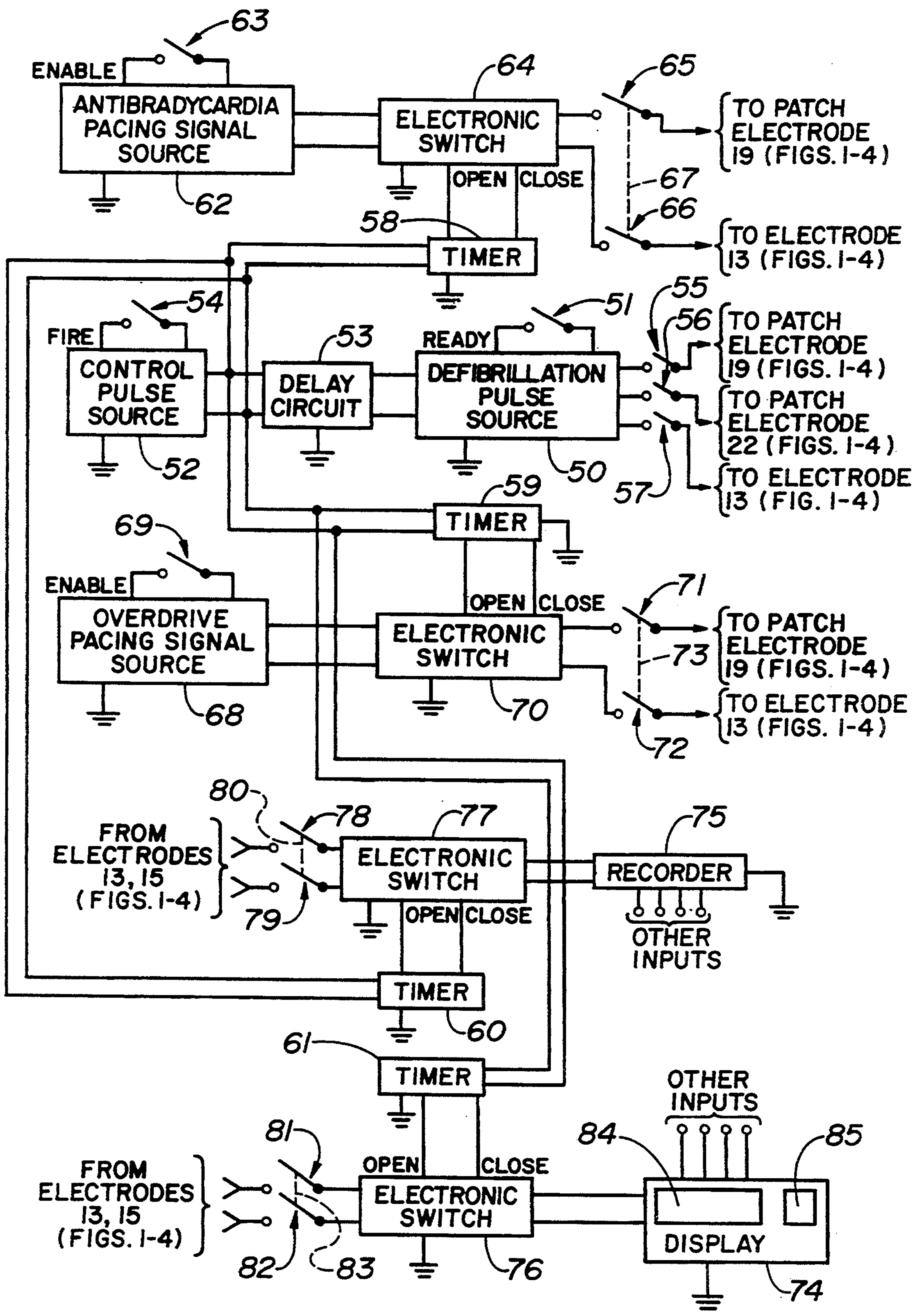
FIG. 5 is a block diagram of a circuit which, when used in conjunction with any of the esophageal probe and electrode arrangements illustrated respectively in FIGS. 1–4, constitutes an exemplary system for defibrillating, pacing and monitoring the heart of a subject in accordance with the present invention.

In the event the subject needs to have his or her heart paced, often the case at least initially subsequent to defibrillation and/or before defibrillation is attempted, pacing signals may be supplied between the first patch electrode 19 and the distally positioned electrode 13 from a pacemaker (not shown) via the leads 17 and 23. Of course, in some cases the pacing signals could be applied between the patch electrode 19 and the electrode 15, as an alternative, or as an additional route. It is to be understood that the pacemaker may be of a multimode type so that different pacing modalities can be selected, such as overdrive pacing or antibradycardia pacing to name two types, depending on the needs of the subject. Alternatively, individual pacemakers supplying differing pacing modalities could be used, as illustrated in FIG. 5.

A portion of the outer surface of the probe 11 may be provided with indicia 25, indicative of the distance, possibly in centimeters, between the electrode 13 and the mouth of the subject 10. Alternatively, the indicia may simply be indicative of the height of the subject, in more generalized terms, such as tall, medium and short for adults. In this case the indicia could be, for example, in the form of broad bands or the like.

In accordance with the present invention as noted above, the distally positioned electrode 13 and the more proximately positioned electrode 15 carried by the probe 11 may be advantageously used to derive ECG signals. Bipolar recordings and/or displays may be effected, using the distally positioned first electrode 13 and the more proximately positioned second electrode 15. The probe 11 may be used in conjunction with a mouthpiece (not shown in FIG. 1) which could be used to guide the probe during insertion.

Figures 2, 2A:
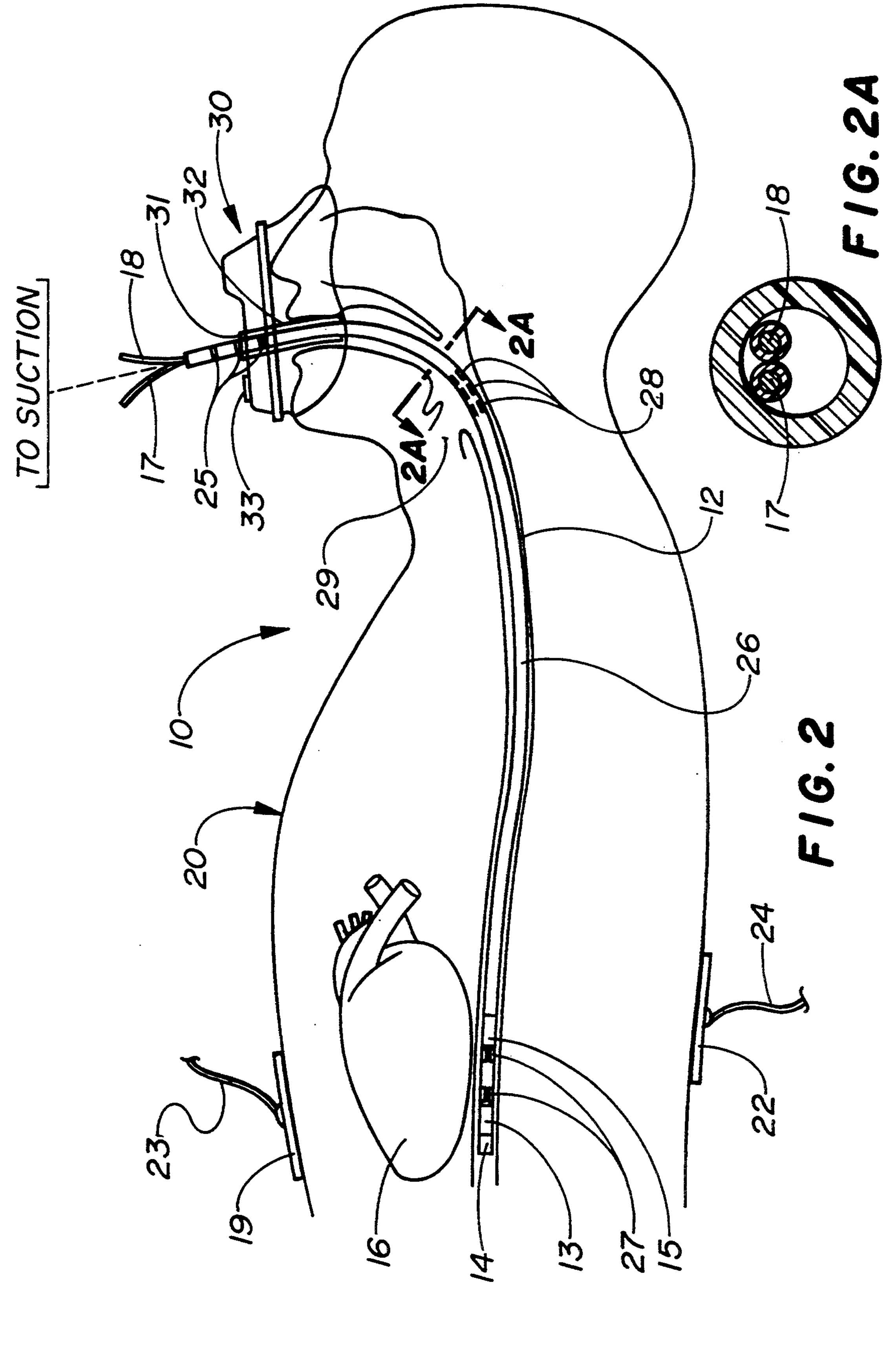
FIG. 2 is a pictorial view of a second embodiment of an esophageal probe and electrode arrangement in accordance with the present invention, in which the probe is hollow so that it may be used to remove contents of the esophagus and/or stomach, the arrangement being suitable for practicing the invention in its system aspect, a patient being shown in phantom.
FIG. 2A is a cross-sectional view of the probe shown in FIG. 2, the section being taken along section line 2A—2A.

As illustrated in FIGS. 2 and 2A, an exemplary second embodiment of the esophageal probe and electrode arrangement is shown pictorially as used with a patient (subject) 10, shown in phantom. The elongated, flexible probe 26, shown positioned within the esophagus 12 of the subject 10 differs primarily from the probe 11 shown in FIG. 1 in that it is hollow. The hollow probe 26 is made of electrically insulative material, such as a plastic, is cylindrical, and has a wall thickness of about one-sixteenth of an inch. The probe 26, like the probe 11 (FIG. 1) carries fixedly on its outer surface a first electrode 13 and a second electrode 15, the electrodes 13 and 15 being sized, shaped and positioned as are the corresponding electrodes 13 and 15, in the first embodiment (FIG. 1). As in the first embodiment, the probe 26 as shown in FIG. 2, includes a first electrically conductive, insulated lead 17 and a second, electrically conductive, insulated lead 18 which extend respectively from beyond the proximal end of the flexible probe 26 to the respective metal electrodes 13 and 15. The surfaces of the leads 17 and 18 have insulation thereon and extend longitudinally within the open space within the hollow probe 26, as best shown in FIG. 2A. The distal ends of the leads 17 and 18 are conductively connected respectively to the electrodes 13 and 15. The leads 17 and 18 respectively provide electrical paths from the respective electrodes 13 and 15. In a monitoring mode, bipolar ECG signals can be supplied from these electrodes. The leads 17 and 18 provide respective possible pacing inputs to the heart 16 of the subject 10 via the respective metal electrodes 13 and 15, the electrode 13, as in the case of the first embodiment, being preferred because it is positioned nearer the ventricular area of the heart 16.

A first conventional, large area, metallic patch electrode 19 is positioned over the anterior of the thorax 20 of the subject 10 in the vicinity of the sternum and a second conventional, large area, metallic patch electrode 22 is shown positioned over a large area of the posterior of the thorax 20 of the subject 10. It is to be appreciated that the second patch electrode 22 is positioned in the position shown whenever a clinician or paramedic elects to effect defibrillation via the transthoracic route, the defibrillating pulse(s) being applied, in this case, between the first patch electrode 19 and the second patch electrode 22. A third, electrically conductive, insulated lead 23 and a fourth, electrically conductive, insulated lead 24 provide respectively electrical connections to the anterior patch electrode 19 and the posterior patch electrode 22.

Were the clinician or paramedic to determine that rescue defibrillation should be attempted via the transesophageal route, the patch electrode 22 would be removed from the subject 10 or disconnected from the defibrillation source (not shown) and the defibrillating pulse or pulses applied between the distal, first electrode 13 and the anterior patch electrode 19.

Were a subject 10 to require his or her heart to be paced, antibradycardiac pacing pulses and/or overdrive pacing signals may be supplied between the first patch electrode 19 and the distally positioned electrode 13 from a pacemaker (not shown) via the leads 17 and 23. In some cases, pacing pulses could be supplied, as an alternative, between the first patch electrode 19 and the electrode 15. It is also contemplated that pacing signals may be supplied between each of the electrodes 13, 15 and the first patch electrode 19.

The distally positioned electrode 13 and the more proximately positioned electrode 15 carried by the probe 11 may also be advantageously used to derive ECG signals, bipolar recordings and/or displays may be realized from the signals, as in the first embodiment (FIG. 1).

The wall of the hollow probe 26 is provided, in the vicinity of its distal end, with a plurality of apertures 27 for the purpose of allowing removal of the contents from the esophagus and/or stomach of the subject 10 by suction. Were the clinician or paramedic to conclude that removal of the contents was necessary or desirable, conventional suction apparatus would be coupled to the distal end of the hollow probe 26 and activated, as required. As shown, the probe 26 is open at its distal end to aid in removal of the contents; however, the distal end may be closed, if desired.

The hollow probe 26 may be provided with a plurality of apertures 28 along a portion of its length for the purpose of allowing air and/or oxygen communication to and from the windpipe 29 of the subject 10, when the probe 26 is in place. In this case, it would be desirable to shield the apertures 28 so that stomach contents do not enter the lungs of the subject 10. If desired, a mask 30 constructed externally similarly to the mask disclosed in U.S. Pat. No. 4,574,807 may be used in conjunction with the hollow probe 26, an opening 31 being provided in the mask 30. A bite tube 32 is fixed in the opening 31 and extends into the mouth of the subject. The probe 26 is inserted into the fixedly positioned bite tube 32 and moved into the mouth of the subject 10 and, thence, into the esophagus 12 of the subject. When positioned for use, as illustrated, a number of the apertures 28 in the probe 26 become positioned adjacent to the windpipe 29 of the subject 10, allowing air to be delivered to the windpipe and expirant to be removed therefrom. The proximal end of the probe 26, which extends above the outer surface of the mask, may be provided with a standard fitting, allowing it to be coupled to a suction apparatus (not shown) were one to desire to remove the contents of the esophagus 12 and/or stomach.

The mask 30 is advantageously provided with a closeable second opening 33 through which a breathing tube (not shown) or the like may be inserted, thus providing the possibility of supplying air and/or oxygen to the subject 10 from ambient or compressed source. Were such a breathing tube to be used, the probe 26 need not be provided with the apertures 28.

Figures 3, 3A:
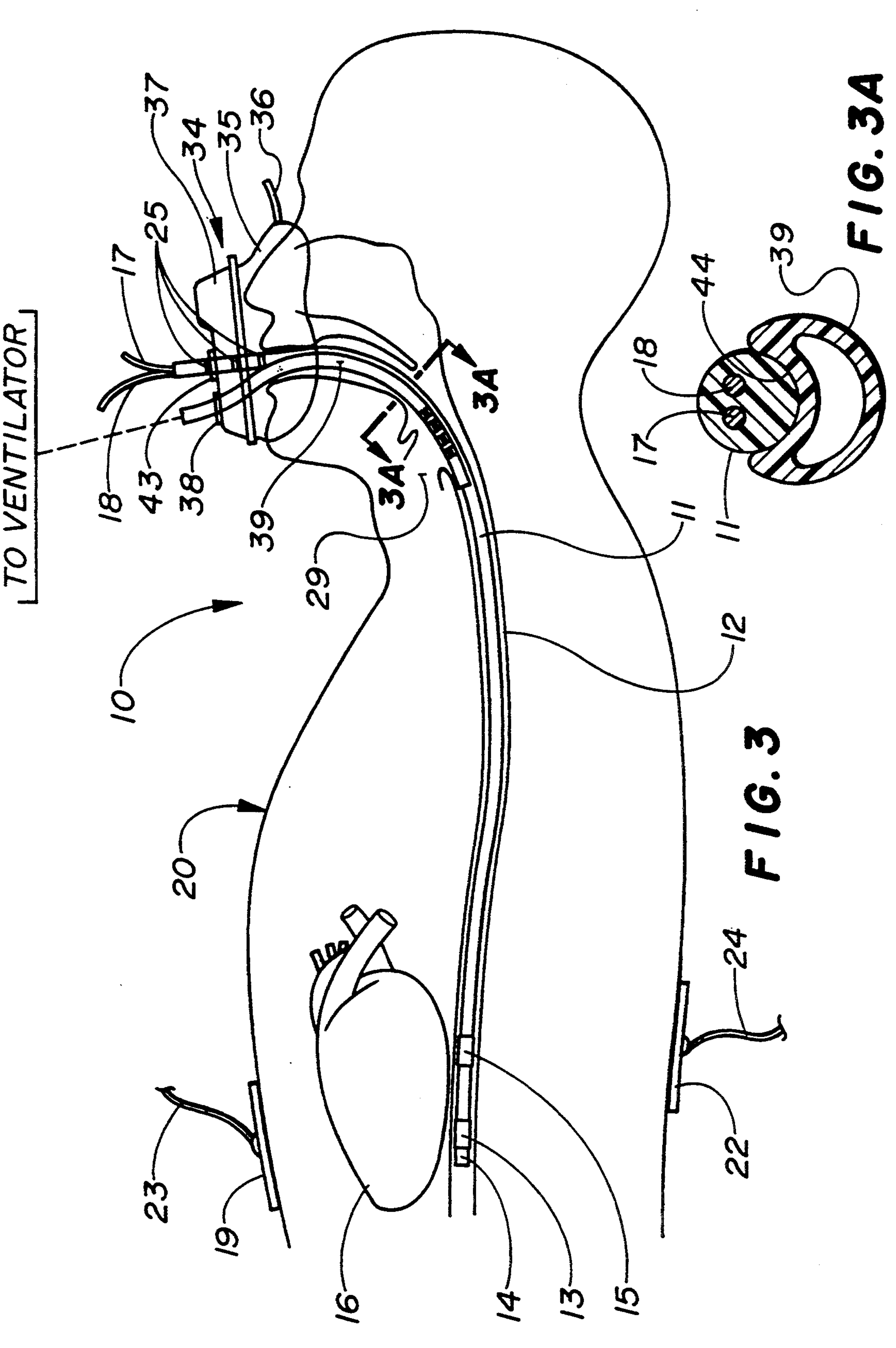
FIG. 3 is a pictorial view of the first embodiment of an esophageal probe and electrode arrangement in accordance with the present invention which may be used in practicing the present invention in its system aspect, used in conjunction with a separable catheter provided for fluid communication, via the windpipe, to and from the lungs of a subject so as to effect conveying of air or oxygen to the lungs and receiving expirant therefrom and which may be used in conjunction with a ventilator, a patient being shown in phantom.
FIG. 3A is a cross-sectional view of the catheter and probe shown in FIG. 3, the section being taken along section line 3A—3A.

As illustrated in FIGS. 3 and 3A, a further exemplary embodiment of a system which includes the esophageal probe and electrode arrangement of FIG. 1 is shown pictorially as used with a patient (subject) 10, shown in phantom. The elongated, flexible probe 11, shown positioned within the esophagus 12 of the subject 10 corresponds to the probe 11 shown in FIG. 1. The probe 11 is made of electrically insulative material, such as a plastic, and is cylindrical in shape.

The probe 11, as shown in FIG. 3 is shown in conjunction with a mask 34 of the type disclosed in U.S. Pat. No. 4,574,807, modifications being provided in accordance with the present invention. The mask 34 covers a substantial portion of the subject's face including the nose and mouth. The mask 34 has an inflatable collar 35 that extends about the entire periphery of the mask, so that the mask may fit tightly against the face of the subject 10. An inflation tube 36 is provided with appropriate valving to enable the collar 35 to be inflated. The mask 34 also is provided with an enlarged portion 37 to accommodate the nose of the subject 10.

A number of openings are provided in the mask 34. One opening 38 is occupied by elongated, hollow, flexible, ventilation tube 39 that extends an inch or more above the outer surface of mask 34 while its other (distal) end 40 extends from inside the mask a sufficient distance when the mask lies against the face, slightly beyond the opening to the windpipe 29 of the subject 10. The proximal end of the ventilating tube 39 may be provided with a standard connector to connect it to a ventilating apparatus (not shown). The ventilating tube 39 is strong enough to prevent the subject 10, when clamping down on it radially, from obstructing flow through a ventilating tube. Thus, the tube 39 also functions as a bite tube, as well as a ventilating tube. The ventilating tube 39 has, in the vicinity of its distal end 40, a plurality of apertures 41 for allowing fluid communication to and from the windpipe 29 of the subject 10.

A second opening 42 in mask 34 adjacent to the opening 38 carries a tubular fitting 43. The inner end of the fitting 43 extends beyond the inner surface of the mask 34 to the vicinity of the outer surface of the hollow ventilation tube 39. The hollow, ventilation tube 39 has along its outer surface a smooth curved surface area 44 (FIG. 3A) which compliments the outer surface of the probe 11, thereby allowing the probe 11 to be inserted through the second opening 42 in the mask 34 and to be guided along the complimentary, curved surface area 44 into the esophagus 12 of the subject 10. The probe 11 carries fixedly on its outer surface a first metal electrode 13 and a second metal electrode 15, the electrodes 13 and 15 being sized, shaped and positioned as are the corresponding electrodes 13 and 15, in the first embodiment (FIG. 1). As in the first embodiment, the probe 11 as shown in FIG. 3, includes a first electrically conductive, insulated lead 17 and a second, electrically conductive, insulated lead 18 which extend respectively from beyond the proximal end of the flexible probe 11 within the probe to the respective metal electrodes 13 and 15. The surfaces of the leads 17 and 18 are insulated. The distal ends of the leads 17 and 18 are conductively connected respectively to the electrodes 13 and 15. The leads 17 and 18 provide an electrical path from the respective electrodes 13 and 15. In a monitoring mode, bipolar ECG signals can be supplied from these electrodes. The leads 17 and 18 provide respective possible pacing inputs to the heart 16 of the subject via the respective metal electrodes 13 and 15, the electrode 13, as in the case of the first embodiment being preferred because it is positioned nearer the ventricular area of the heart 16.

A first conventional, large area, metallic patch electrode 19 is positioned over the anterior of the thorax 20 of the subject 10 in the vicinity of the sternum and a second conventional, large area, metallic patch electrode 22 is shown positioned over a large area of the posterior of the thorax 20 of the subject 10. It is to be appreciated that the second patch electrode 22 is placed in the position shown whenever a clinician or paramedic elects to effect defibrillation via the transthoracic route, in this case the defibrillating pulse(s) being applied between the first patch electrode 19 and the second patch electrode 22. A third, electrically conductive, insulated lead 23 and a fourth, electrically conductive, insulated lead 24 provides respectively electrical connections to the anterior patch electrode 19 and the posterior patch electrode 22.

Were the clinician or paramedic to determine that rescue defibrillation should be attempted via the transesophageal route, the patch electrode 22 would be removed from the subject or disconnected from the defibrillation source (not shown) and the defibrillating pulse or pulses applied between the distal, first electrode 13 and the anterior patch electrode 19.

Were a subject to require his or her heart to be paced, pacing pulses and/or overdrive pacing signals may be supplied between the first patch electrode 19 and the distally positioned electrode 13 from a pacemaker (not shown) or pacemakers (not shown) via the leads 17 and 23. As in the embodiments illustrated in FIGS. 1 and 2, pacing pulses and/or overdrive signals may also be supplied between the first patch electrode 19 and the electrode 13. In some cases, distinct, respective pacing signals may be supplied between the patch electrode 19 and the respective electrodes 13 and 15.

The distally positioned electrode 13 and the more proximately positioned electrode 15 carried by the probe 11 may also be advantageously used to derive ECG signals, bipolar recordings and/or displays may be effected, as in the first embodiment (FIG. 1).

Figures 4, 4A:
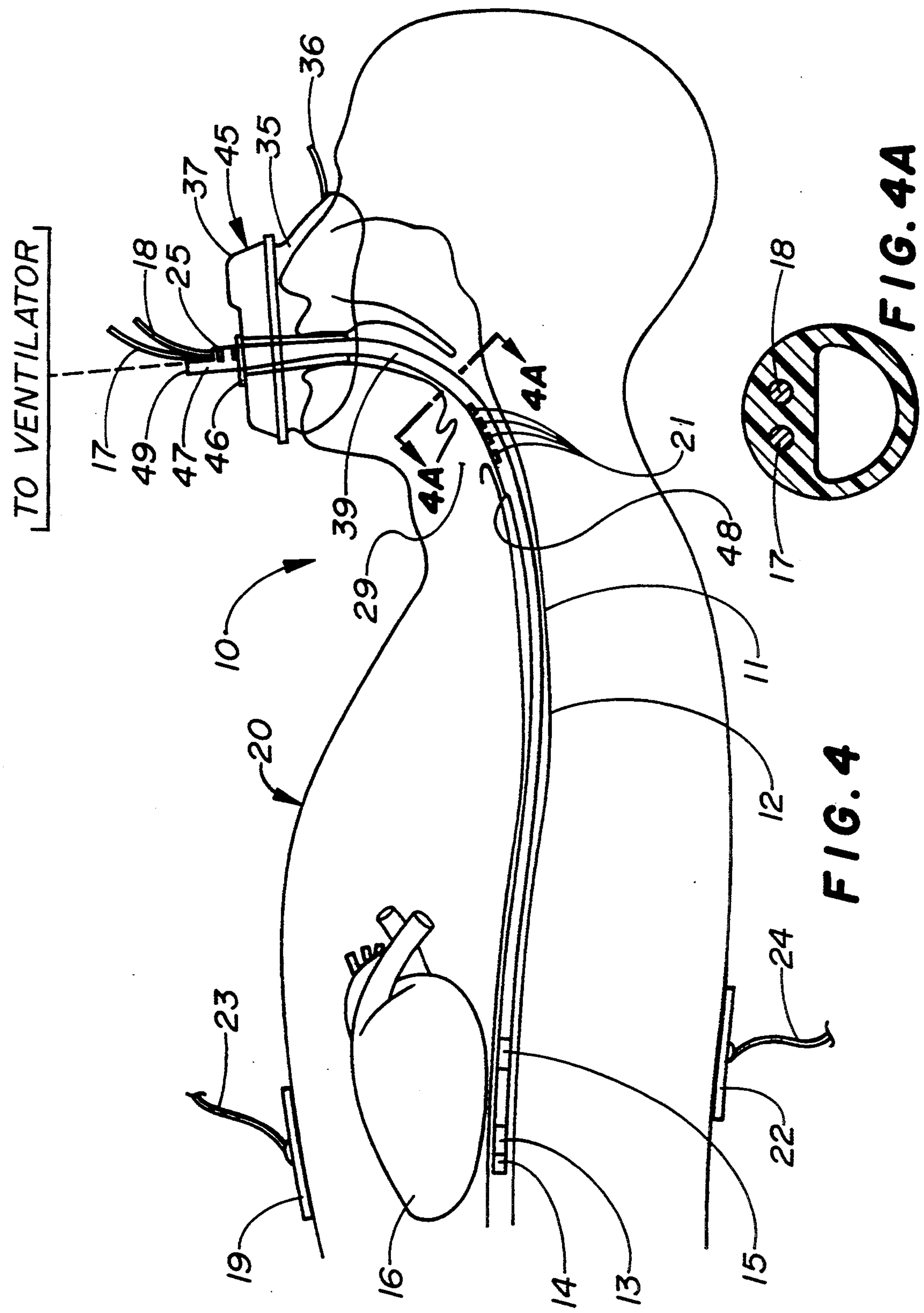
FIG. 4 is a pictorial view of a variant of the system shown in FIG. 3 in which the probe is integral with the catheter for conveying air or oxygen to the windpipe and receiving expirant therefrom, possibly in conjunction with a ventilator, a patient being shown in phantom.
FIG. 4A is a cross-sectional view of the integral catheter and probe shown in FIG. 4, the section being taken along section line 4A—4A.

As illustrated in FIG. 4, a further exemplary embodiment of a system which includes the esophageal probe and electrode arrangement of FIG. 1 is shown pictorially as used with a patient (subject) 10, shown in phantom. The elongated, flexible probe 11, shown positioned within the esophagus 12 of the subject 10, corresponds to the probe 11 shown in FIG. 1. The probe 11 is made of electrically insulative material, such as a plastic, and is cylindrical in shape.

The probe 11, as shown in FIG. 4 and FIG. 4A is shown in conjunction with a mask 45 of the type disclosed in U.S. Pat. No. 4,574,807, modifications being provided in accordance with the present invention. The mask 45 covers a substantial portion of the subject's face including the nose and mouth. The mask 45 has an inflatable collar 35 that extends about the entire periphery of the mask, so that the mask may fit tightly against the face of the subject 10. An inflation tube 36 is provided with appropriate valving to enable the collar 35 to be inflated. The mask 45 also is provided with an enlarged portion 37 to accommodate the nose of the subject 10.

An opening is provided in the mask 45. The opening 46 is occupied by the probe 11 and an elongated, hollow, flexible, ventilation tube 47 that extends an inch or more above the outer surface of mask 45 while its other (distal) end 48 extends from inside the mask a sufficient distance when the mask lies against the face, slightly beyond the opening to the windpipe 29 of the subject 10. The proximal end 49 of the ventilating tube 47 may be provided with a standard connector to connect it to a ventilating apparatus (not shown). The ventilating tube 47 is strong enough to prevent the subject 10, when clamping down on it radially, from obstructing flow through the ventilating tube. Thus, the tube 47 also functions as a bite tube, as well as a ventilating tube. The ventilating tube 47 has, in the vicinity of its distal end 48, a plurality of apertures 21 for allowing fluid communication to and from the windpipe 29 of the subject 10.

The hollow, ventilation tube 47 is integral with the probe 11, as shown in FIG. 4A, thereby allowing the probe 11 and the tube 47 to be placed in operative position within the subject 10 at the same time. The probe 11 carries fixedly on its outer surface a first metal electrode 13 and a second metal electrode 15, the electrodes 13 and 15 being sized, shaped and positioned as are the corresponding electrodes 13 and 15, in the first embodiment (FIG. 1). As in the first embodiment, the probe 11 as shown in FIG. 4, includes a first electrically conductive, insulated lead 17 and a second, electrically conductive, insulated lead 18 which extend respectively from beyond the proximal end of the flexible probe 11 within the probe to the respective metal electrodes 13 and 15. The surfaces of the leads 17 and 18 are insulated. The distal ends of the leads 17 and 18 are conductively connected respectively to the electrodes 13 and 15. The leads 17 and 18 provide an electrical path from the respective electrodes 13 and 15. In a monitoring mode, bipolar ECG signals can be supplied from these electrodes. The leads 17 and 18 provide respective possible pacing inputs to the heart 16 of the subject via the respective metal electrodes 13 and 15, the electrode 13, being preferred because it is positioned nearer the ventricular area of the heart 16.

A first conventional, large area, metallic patch electrode 19 is positioned over the anterior of the thorax 20 of the subject 10 in the vicinity of the sternum and a second conventional, large area, metallic patch electrode 22 is shown positioned over a large area of the posterior of the thorax 20 of the subject 10. It is to be appreciated that the second patch electrode 22 is placed in the position shown whenever a clinician or paramedic elects to effect defibrillation via the transthoracic route, in this case the defibrillating pulse(s) being applied between the first patch electrode 19 and the second patch electrode 22 A third, electrically conductive, insulated lead 23 and a fourth, electrically conductive, insulated lead 24 provides respectively electrical connections to the anterior patch electrode 19 and the posterior patch electrode 22.

Were the clinician or paramedic to determine that rescue defibrillation should be attempted via the transesophageal route, the patch electrode 22 would be removed from the subject or disconnected from the defibrillation source (not shown) and the defibrillating pulse or pulses applied between the distal, first electrode 13 and the anterior patch electrode 19.

Were a subject to require his or her heart to be paced, to pacing pulses and/or overdrive pacing signals may be supplied between the first patch electrode 19 and the distally positioned electrode 13 from a pacemaker (not shown) via the leads 17 and 23. As in the embodiments illustrated in FIGS. 1 and 2, passing pulses and/or overdrive signals may also be supplied between the first patch electrode 19 and the electrode 13. In some cases, distant, respective pacing signals may be supplied between the patch electrode 19 and the respective electrodes 13 and 15.

The distally positioned electrode 13 and the more proximately positioned electrode 15 carried by the probe 11 may also be advantageously used to derive ECG signals, bipolar recordings and/or displays may be effected, as in the first embodiment (FIG. 1).

With reference to FIG. 5, an exemplary circuit, which may be used in conjunction with the esophageal probe and electrode arrangements of FIGS. 1–4, includes a defibrillation pulse source 50 having an associated manually operated, single-pole, single-throw, ready switch 51 which, when closed, enables power to be supplied to circuits within the defibrillation pulse source 50 and allows its energy storing capacitor(s) to be charged. The defibrillation pulse source 50 may include conventional voltage and charge level setting circuitry, allowing a clinician or paramedic to set voltage and energy levels to suit the subject. A control signal source 52 has its output coupled to the control input of the defibrillation pulse source 50 via a time delay circuit 53, which provides a brief time delay of, for example, two seconds. Of course, the time delay may be longer or considerably shorter in duration. The purpose of the time delay is to protect other circuit components from damage by the high voltage, large energy pulse(s) which are to be supplied to the subject from the defibrillation pulse source 50, via its three output terminals, respective independent, manually operated, single-pole single-throw switches 55, 56, 57, and either electrode pair 19, 22 or electrode pair 19, 13. The control pulse source 52 is provided with a manually operated, single-pole single-throw, fire control switch 54 which, when momentarily closed causes the control pulse source to produce a control pulse which is fed to the defibrillation pulse source 50 via the delay circuit 53. The delayed control pulse effects the firing of he defibrillation pulse source 50 provided the ready switch 51 has been closed.

As illustrated, the output pulse fed from the control pulse source 52 is also fed, without delay, to the control inputs of four timers 58, 59, 60 and 61.

The exemplary circuit includes an antibradycardia pacing signal source 62 provided with a manually operated, single-pole, single-throw, enable switch 63 which, upon being closed by a clinician or paramedic, enables the source 62 to produce pacing pulses. The pacing pulses are fed, via a normally closed electronic switch 64, its respective signal output terminals and respective manually operated, single-pole, single-throw switches 65, 66, to respective patch electrode 19 (FIGS. 1–4) and metal electrode 13 (FIGS. 1–4) via leads. As shown, the switches 65 and 66 are ganged together, as indicated by dashed-line 67. The normally closed electronic switch 64 has two input control terminals, respectively labeled OPEN and CLOSE in FIG. 5, control signals being supplied to the switch from respective outputs of the timer 58. In operation, the timer 58, upon receipt of a control pulse from the control pulse source 52, produces an output control signal to the OPEN signal input terminal of the electronic switch 64 which control signal effects the opening of this switch, thereby protecting the pacing signal source 62 from possible damage during application of the high voltage, large energy pulse(s) from the defibrillation pulse source 50. The timer 58 holds the electronic switch 64 OPEN for a given period of time, for example, one-half a second or slightly longer than the duration of the defibrillation pulse. At the end of the OPEN period, the timer 58 produces a second output control signal which is fed to the CLOSE signal input terminal of the electronic switch 64, allowing this switch to return to its normally closed condition.

The exemplary circuit of FIG. 5 includes an overdrive pacing signal source 68 having a manually operated, single-pole, single-throw, enable switch 69 which, upon being closed by a clinician or paramedic, enables the source 68 to produce overdrive pacing signals. The overdrive pacing signals are fed, via a normally closed electronic switch 70, its respective signal output terminals and respective manually operated, single-pole, single-throw switches 71, 72, to respective patch electrode 19 (FIGS. 1–4) and metal electrode 13 (FIGS. 1–4) via leads. The switches 71 and 72 are ganged together, as shown diagrammatically by dashed-line 73. The normally closed electronic switch 70 is provided with two input control terminals, respectively labeled OPEN and CLOSE in FIG. 5, control signals being supplied to this switch from respective outputs of the timer 59. In operation, the timer 59, upon receipt of an undelayed control pulse from the control pulse source 52, produces an output control signal to the OPEN signal input terminal of the electronic switch 70 which control signal effects the opening of this switch, thereby protecting the overdrive pacing signal source 68 from possible damage during application of the high voltage, large energy pulse(s) from the defibrillation pulse source 50. The timer 59 holds the electronic switch 70 OPEN for a given period of time, for example, one-half a second or slightly longer than the duration of the defibrillation pulse during its delivery. At the end of the OPEN period, the timer 59 produces a second output control signal which is fed to the CLOSE signal input terminal of the electronic switch 70, allowing this switch to return to its normally closed condition.

The circuit of FIG. 5 is advantageously provided with a display 74 and a recorder 75. The display 74 and the recorder 75 are provided with respective pairs of bipolar input terminals operatively arranged to receive ECG signals from electrodes 13, 15 (FIGS. 1–4) via leads and the respective normally closed electronic switches 76 and 77. The electronic switches 76 and 77 each have switching control signals input terminals labeled OPEN and CLOSE, these terminals being connected to control signal output terminals of the respective timers 61 and 60. The input signals to the timers 60 and 61 consist of the undelayed output pulse signal from the control pulse source 52. The electronic switches 76 and 77, in operation in conjunction with the respective timers 61, 60, effectively disconnect respectively the display 74 and the recorder 75 from the electrodes 13, 15 (FIGS. 1–4) during a period slightly longer than the duration of the defibrillation pulses. Thus, the circuitry within the display 74 and the recorder 75 may be protected from damage from the defibrillation pulse(s).

If desired, manually operated, single-pole, single-throw, switches 78 and 79 may be provided in the input signal paths from the electrodes 13, 15 (FIGS. 1–4) and associated leads to the electronic switch 77, so that a clinician or paramedic may elect either to record or not to record ECG signals from the electrodes 13, 15. The switches 78 and 79 may advantageously be ganged together, as indicated by the dashed-line 80, to simplify set up. In some cases, however, these switches should not be ganged together, were one to desire to record signals derived from one or the other of the electrodes 13, 15 (FIGS. 1–4) and, for example, a conventional external body surface electrode (not shown). Manually-operated, single-pole, double-throw switches 81 and 82, illustrated as possibly ganged by dashed-line 83, may be provided in the input lines to the electronic switch 76.

The display 74 and the recorder 75 may be provided with other inputs, such as inputs reflecting the vital signs and other ECG signals from body surface electrodes. The display 74 may include a screen 84 to display ongoing wave forms and an LED 85 display which could display current vital sign data, mean blood pressure, systolic blood pressure, diastolic blood pressure and the like in numerical form.

In practicing the present invention, as illustrated, the clinician or paramedic would position the probe and electrodes of the present invention in the positions shown in any one of the FIGS. 1–4. He would then electrically connect the electrodes to the circuitry of FIG. 5 as indicated by text, were the connections not already made. After deciding the therapy or therapies to use, as well as which pairs of electrodes are to be used for defibrillation, he or she would close the relevant ones of the manually-operated switches shown in FIG. 5. Using the manually-operated switches shown in FIG. 5, during set up or in the course of treatment, he or she may elect to enable one or the other of the pacing functions or none of these or one after the other, to make ready the defibrillation pulse source, to select the pair of electrodes for applying the defibrillation pulse(s) and to select the other pair later, if needed, to fire the defibrillation pulse source, and to select either or both of the recording and display functions.

Materials and Methods

Fourteen mongrel dogs of either sex weighing 20 to 30 kg were used in a recent study in which an esophageal probe constructed in accordance with the present invention was used. The first 10 dogs were investigated as part of an acute feasibility and efficacy study; and an additional four dogs underwent chronic studies primarily to assess the safety of this technique. All animals were sedated with fentanyl (0.04 mg/kg) and droperidol (2 mg/kg), anesthetized with intravenous sodium pentobarbital (7–12 mg/kg), and mechanically ventilated. Two stainless steel electrodes with a large surface area (300 $mm^2$) were mounted 8 cm apart on an esophageal probe and inserted approximately 40 cm from the mouth. Defibrillation testing was performed in the following manner. The system included two large proximal and distal electrodes. The system was compatible with standard emergency room defibrillators as well as external transcutaneous pacing systems. Both esophageal pacing and defibrillation were accomplished using identical configurations (i.e., distal electrode is the anode and anterior skin patch is the cathode). AC current was delivered via a transvenous right ventricular pacing lead to the myocardium in order to provoke ventricular fibrillation (VF). Using a standard defibrillator (Lifepak 6, Physio-Control, Redmond, Wash.), high energy was used to deliver a monophasic wave form both transthoracically and transesophageally. A preliminary series of three animal experiments were performed to define the optimal defibrillation configuration for the study. After testing a variety of electrode configurations, defibrillation between the distal esophageal electrode (anode) and an anterior skin patch (cathode) resulted in reproducible successful termination of induced VF.

Transesophageal defibrillation was compared to transthoracic defibrillation in 14 dogs using a paired T test. A P valve $<0.05$ was arbitrarily considered as statistically significant. After 15 seconds of induced VF, transesophageal and transthoracic defibrillation thresholds (DFT) were determined in random order. Transthoracic defibrillation was performed using standard defibrillator paddles placed at the level of the myocardium on both sides of the chest. DFT was defined by the two lowest successful energy levels for defibrillation without a failure. DFT testing was performed by a test and rescue shock sequence, with 5 minutes between test shocks. The initial test shock was 50 Joules. If successful, 30 and 20 Joules were tested. If the lowest successful energy was 20 Joules, this was repeated and if successful, the DFT was considered to be 20 Joules. If unsuccessful, 30 Joules was then tested and if successful, the DFT was considered to be 30 Joules. If the initial 50 Joule shock was unsuccessful, a rescue shock was delivered and 100, 200, and 300 Joules were tested until two consecutive successful values were obtained. In addition, transesophageal bipolar signals (proximal to distal electrode) were recorded and transesophageal pacing threshold was determined immediately prior to DFT testing using the identical configuration as that used for defibrillation. After determination of both pacing threshold and DFT, esophageal electrode location was visualized via fluoroscopy and recorded on VHS tape.

Histopathological examinations were performed in 10% formalin fixed paraffin sections of excised dog esophagi. Esophagi were sequentially sectioned from the proximal to distal ends. The sections were stained with hematoxylin and eosin. Multiple sections and each esophagus were examined microscopically and graded for severity of injury using the following criteria: (A) disruption of submucosal glands with inspissated mucus, (B) disruption of mucosa, (C) coagulative necrosis of muscle fibers with disruption of fibers and clumping of cytoplasm, and (D) loss of muscle fibers. Esophagi were coded and blindly interpreted by a pathologist, who graded the severity of each of the lesions from 1 to 4 for each of the above criteria. A combined total of 4 indicated no specific pathological abnormality, whereas 16 indicated the most severe pathologic abnormality.

Results of Animal Studies

Figure 6:
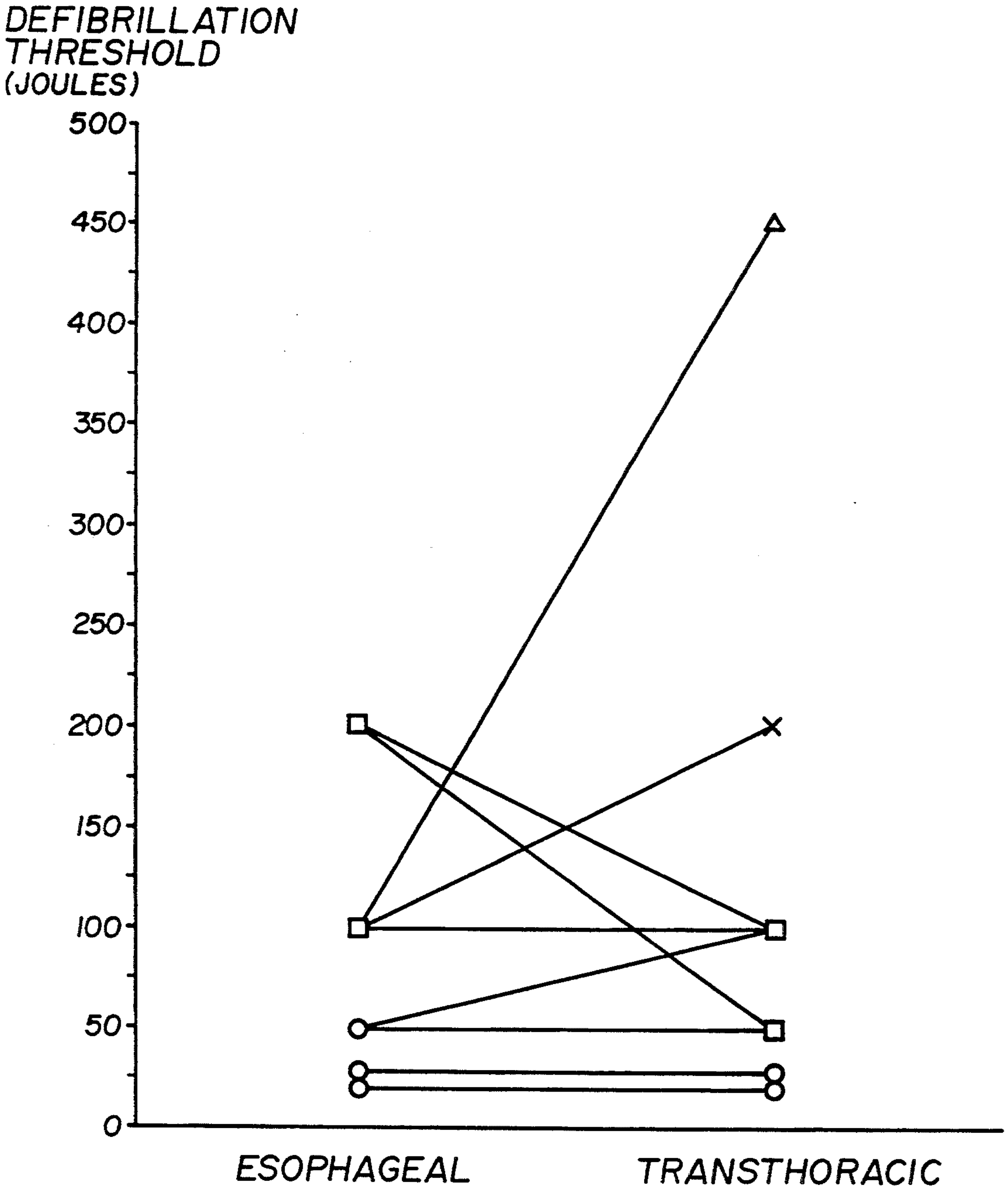
FIG. 6 shows the defibrillation thresholds (DFTs) obtained in each of a number of animals by both transesophageal and transthoracic defibrillation, during initial animal studies.
Figure 7:
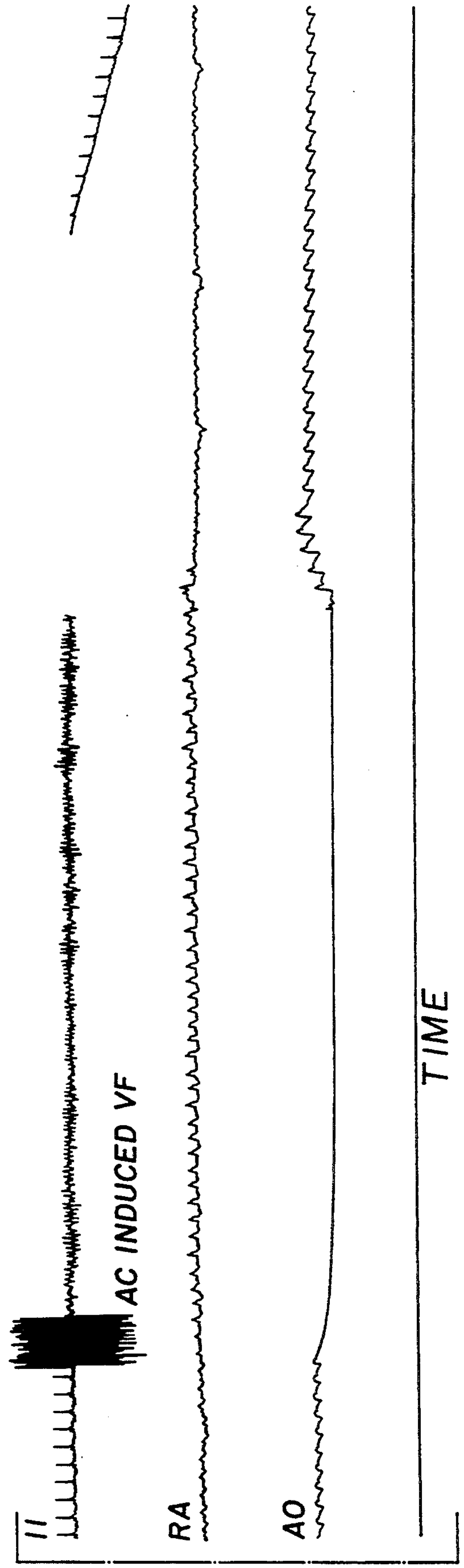
FIG. 7 shows graphical representations of simultaneous recordings of lead II, right atrial pressure (RA) and aortic pressure during transesophageal defibrillation, made in conjunction with the animal studies.

The distal electrode (anode) and anterior skin patch (cathode) configuration was universally successful in terminating ventricular fibrillation. FIG. 6 shows the defibrillation thresholds (DFTs) obtained in each animal by both esophageal and transthoracic methods. FIG. 6 shows the DFTs obtained in each animal by both transesophageal and transthoracic defibrillation. Esophageal DFTs (mean=±15 Joules) tended to be lower than transthoracic DFT (115±35 Joules), though this difference was not statistically significant. FIG. 7 shows an ECG tracing of transesophageal defibrillation. FIG. 7 shows simultaneous recordings of lead II, right atrial pressure (RA) and aortic pressure during transesophageal defibrillation. The top panel shows ventricular fibrillation induced by AC current. Fifty Joules delivered from the distal esophageal electrode to an anterior skin patch successfully terminated ventricular fibrillation. Fifty Joules delivered between the distal esophageal electrode and the anterior skin patch was successful in terminating ventricular fibrillation. Transesophageal DFT (90±115 Joules) tended to be lower than transthoracic DFT (115±35 Joules), though this difference was not statistically significant. In addition, one dog with refractory ventricular fibrillation could not be defibrillated by the transthoracic approach (up to 500 Joules), but responded to transesophageal defibrillation. During the animal study, the fluoroscopic position of the transesophageal defibrillation probe in one of the animals was determined. This position relative to the ventricles was typical in all dogs after blind esophageal intubation of the probe; only minor variation in this position was observed (±1 cm) with blind probe placement. A one cm standard deviation in location of the distal electrode as measured from the base of the heart was observed.

Gross and Microscopic Histopathology

In 10 dogs (total energy of 600±150 Joules; range of 250–1600 Joules), none of the esophagi showed grossly detectable damage, and in all cases the mucosa appeared intact. Microscopically, the degree of acute injury demonstrated in the 10 esophagi correlated with the total energy applied ($r=0.70$). One exception was an animal that received only 250 Joules but had moderately severe acute injury (histological grade 14). All of the four long term animals (4 weeks post defibrillation, total energy of 470±110 Joules; range of 130–600 Joules) showed minimal or no residual injury or scarring.

Transesophageal Pacing and Electrograms

Figure 8:
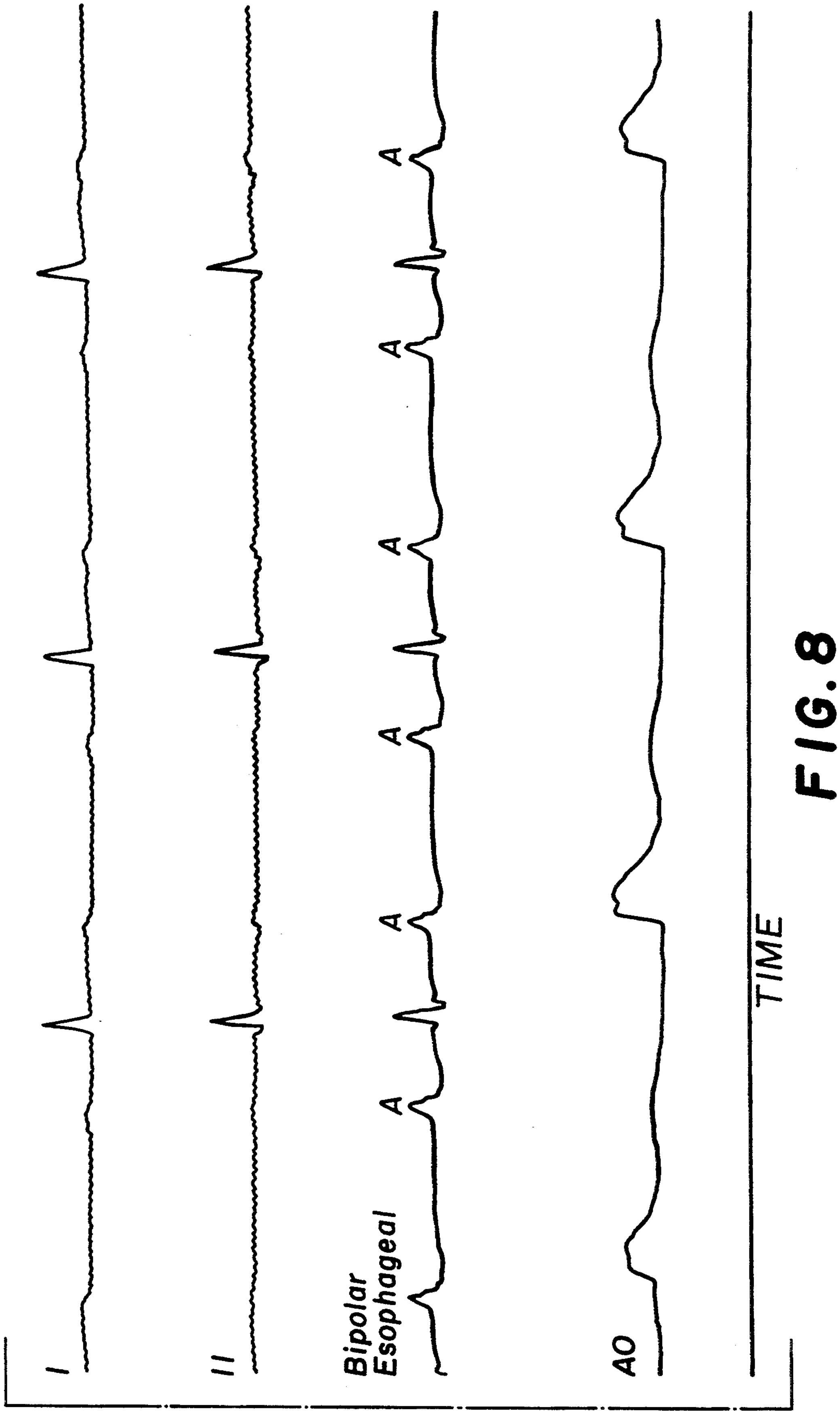
FIG. 8 shows a bipolar esophageal recording which demonstrates second degree AV block post defibrillation.
Figure 9:
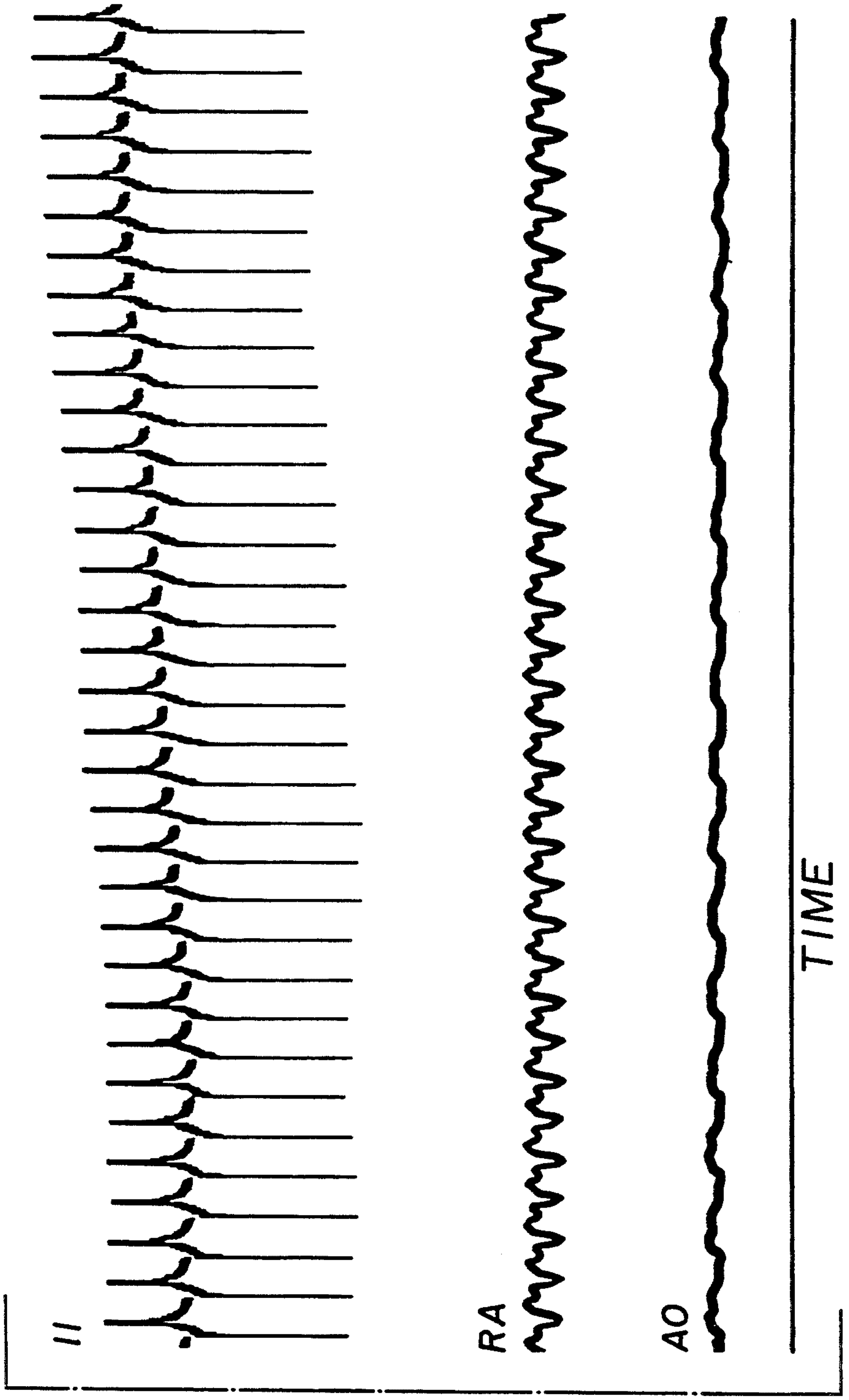
FIG. 9 shows an ECG demonstrating ventricular transesophageal pacing using the identical probe configuration used for defibrillation.

Bipolar recordings using the proximal and distal esophageal electrodes were also useful for arrhythmia discrimination. In each animal, clear atrial and ventricular electrograms were identified. FIG. 8 shows a bipolar recording esophageal recording which demonstrates second degree AV block post defibrillation, aortic pressure (AO) and ECG waveforms from leads I, II being shown as well. Such recordings may prove useful for arrhythmia analysis in critical care patients. Evidence of second degree AV block was identified on both surface and esophageal electrograms in one animal (FIG. 8). FIG. 9 shows an ECG demonstrating ventricular transesophageal pacing using the identical configuration used for defibrillation. Transesophageal pacing had a mean overall threshold of 38±5 mA at a pulse duration of 2.5 ms. Right atrial pressure (RA) and aortic pressure (AO) are also shown in FIG. 9. Transesophageal pacing of the ventricle was accomplished in each animal using a high energy pacing system (Bloom Associates, Inc. Redding, Pa.) with fixed voltage at a pulse width of 2.5 ms and the identical configuration as that used for defibrillation (FIG. 9). Esophageal pacing with this method had a mean threshold of 38±5 mA at a pulse duration of 2.5 ms.

Results of Human Studies

The above-noted techniques have recently been applied in four human patients as a last resort, using an esophageal probe arranged in accordance with the present invention after a prolonged, unsuccessful, conventional cardiopulmonary resuscitation (approximately 50 minutes). Entry criteria, in an approved human study using a system in accordance with the present invention, included the presence of refractory ventricular fibrillation despite at least 3 high energy (≧360 Joules) transthoracic defibrillation attempts. The standard protocol involved use of 3 transesophageal attempts at defibrillation with 100, 200, and then 300 Joules. If the patient failed to convert after 300 Joules, no further shocks were to be administered and standard advanced cardiac life support continued. The etiology of arrest was unknown in 2 patients, narcotic overdose in 1, and end-stage heart failure in 1. Table I below shows the characteristics of each of these patients. In 3 of the 4 patients, transesophageal defibrillation promptly converted ventricular fibrillation to a sinus or wide complex rhythm, however hemodynamic stability could not be restored (electromechanical dissociation). In one patient only a brief period of asystole resulted after the third transesophageal defibrillation. Postmortem examination was not obtained in any of these patients.

TABLE I

Preliminary Clinical Trials with Transesophageal Defibrillation

| Patient | Age/Sex | Transthoracic | Transesophageal | Result |
|---|---|---|---|---|
| 1 | 40 M | 7 | 1 (30J) | Terminated VF to: wide complex tachycardia |
| 2 | 48 F | 6 | 3 (100/200/300J) | wide complex sinus rhythm |
| 3 | 65 F | 5 | 3 (100/200/300J) | asystole back to ventricular fibrillation |
| 4 | 55 M | 5 | 3 (100/200/300J) | wide complex sinus rhythm |

Summary of Results

Blind esophageal probe placement in intubated animals permitted successful termination of ventricular fibrillation and was at least as effective as transthoracic defibrillation. One dog could not be defibrillated by transthoracic defibrillation but responded to transesophageal defibrillation. The DFTs obtained via transesophageal defibrillation were not significantly different than those obtained via transthoracic means. However, the narrow keel-shaped canine chest provides a low transthoracic impedance, quite unlike the human thoracic. The defibrillation probe utilizes an electrode with a large surface area in order to minimize the current density of high energy defibrillation, and thereby minimize esophageal injury. Histopathologic examination of the canine esophagus revealed evidence of acute focal injury with chronic repair (but no evidence of perforation or stricture formation). The esophageal response appeared dose dependent, and safe up to a total energy of 600 Joules.

The above-noted preliminary human studies have demonstrated that transesophageal defibrillation can abort or terminate ventricular fibrillation which failed to respond to multiple high energy transthoracic shocks. it should be emphasized that this technique was tested very late (≧50 minutes) after cardiac arrest. Although transesophageal defibrillation resulted in the termination of ventricular fibrillation in each case, there were no survivors. Earlier implementation of this technique during cardiac arrest appears to be desirable.

The transesophageal defibrillator probe is compatible with standard transthoracic pacing and defibrillating equipment and can record atrial and ventricular electrograms and can be used for cardiac pacing from the esophagus. In the post or intraresuscitating period, often times a variety of arrhythmias appear which are very difficult to define. Hence, transesophageal defibrillation probe would be expected to be very helpful for diagnosis. In addition, it may help treat bradyarrhythmias (by ventricular pacing) and for overdrive pacing termination of ventricular tachycardia and certain types of supraventricular tachycardias.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. A system for defibrillating a malfunctioning heart of a subject having lungs, a throat, a trachea, an esophagus, a stomach and a thorax defined in part by an anterior and a posterior, the system comprising a probe having a proximal end and a distal end, at least a portion of said probe being positionable within the esophagus of the subject; a first electrode carried by said probe in vicinity of said distal end; a second electrode carried by said probe and spaced from said first electrode and at a greater distance from said distal end than said first electrode, said first electrode and said second electrode being electrically distinct from one another; a first patch electrode positionable over a portion of the anterior of the thorax of the subject; a second patch electrode positionable over a portion of the anterior of the thorax of the subject; a source of electrical defibrillating pulses having an output; means for alternatively coupling said output from said source of electrical defibrillating pulses between said first patch electrode and said second patch electrode and between said first patch electrode and one of said electrodes carried by said probe; at least one source of pacing signals having a pacing output; means for coupling said pacing output between one of said electrodes carried by said probe and said first patch electrode; sensing means for sensing electrical activity of the heart; and means for coupling and uncoupling said sensing means between said first electrode and said second electrode carried by said probe.

2. The system according to claim 1, wherein said means for coupling said output from said source of electrical defibrillating pulses alternatively couples said source between said first patch electrode and said second patch electrode and between said first patch electrode and said first electrode carried by said probe in vicinity of said distal end.

3. The system according to claim 2, wherein said sensing means for sensing electrical activity of the heart includes display means for displaying an electrocardiogram representing sensed electrical activity of the heart.

4. The system according to claim 2, wherein said sensing means for sensing electrical activity of the heart includes recording means for recording an electrocardiogram representing sensed electrical activity of the heart.

5. The system according to claim 4, wherein said sensing means for sensing electrical activity of the heart further includes display means for displaying an electrocardiogram representing sensed electrical activity of the heart.

6. The system according to claim 1, wherein said sensing means for sensing electrical activity of the heart includes display means for displaying an electrocardiogram representing sensed electrical activity of the heart.

7. The system according to claim 1, wherein said sensing means for sensing electrical activity of the heart includes recording means for recording an electrocardiogram representing sensed electrical activity of the heart.

8. The system according to claim 7, wherein said sensing means for sensing electrical activity of the heart further includes display means for displaying an electrocardiogram representing sensed electrical activity of the heart.

9. The system according to claim 1, wherein said probe is hollow allowing passage of contents from the esophagus and/or the stomach of the subject into said probe.

10. The system according to claim 9, including means for removing the contents from said probe.

11. The system according to claim 1, wherein said probe is approximately one-half an inch in diameter, said first electrode and said second electrode are each approximately one and one-eighth inches long and are spaced apart from one another by approximately two and five-eighths inches.

12. A system for defibrillating a malfunctioning heart of a subject having lungs, a throat, a trachea, an esophagus and a thorax defined in part by an anterior and a posterior, the system comprising a probe having a distal end and a proximal end, at least a portion of said probe being positionable within the esophagus of the subject; a first electrode carried by said probe in vicinity of said distal end; a second electrode carried by said probe and spaced from said first electrode and at a greater distance from said distal end than said first electrode, said first electrode and said second electrode being electrically distinct from one another; a first patch electrode positionable over a portion of the anterior of the thorax of the subject; a second patch electrode positionable over a portion of the thorax of the subject; a source of electrical defibrillating pulses having an output; means for alternatively coupling said output from said source of defibrillating pulses between said first patch electrode and one of said first electrode and said second electrode carried by said probe, and between said first patch electrode and said second patch electrode; at least one source of pacing signals having a pacing output; means for coupling said pacing output between one of said electrodes carried by the probe and said first patch electrode; sensing means for sensing electrical activity of the heart; and means for coupling and uncoupling said sensing means between said first electrode and said second electrode carried by said probe.

13. The system according to claim 12, wherein said means for coupling said output from said source of electrical defibrillating pulses alternatively couples said source of defibrillating pulses between said first patch electrode and said second patch electrode and between said first patch electrode and said first electrode carried by said probe in vicinity of said distal end.

14. The system according to claim 13, wherein said sensing means for sensing electrical activity of the heart includes display means for displaying an electrocardiogram representing sensed electrical activity of the heart.

15. The system according to claim 13, wherein said sensing means for sensing electrical activity of the heart includes recording means for recording an electrocardiogram representing sensed electrical activity of the heart.

16. The system according to claim 15, wherein said sensing means for sensing electrical activity of the heart further includes display means for displaying an electrocardiogram representing sensed electrical activity of the heart.

17. The system according to claim 12, wherein said sensing means for sensing electrical activity of the heart includes display means for displaying an electrocardiogram representing sensed electrical activity of the heart.

18. The system according to claim 12, wherein said sensing means for sensing electrical activity of the heart includes recording means for recording an electrocardiogram representing sensed electrical activity of the heart.

19. The system according to claim 18, wherein said sensing means for sensing electrical activity of the heart further includes display means for displaying an electrocardiogram representing sensed electrical activity of the heart.

20. The system according to claim 12, wherein said probe is hollow allowing passage of contents from the esophagus and/or the stomach of the subject into said probe.

21. The system according to claim 20, including means for removing the contents from said probe.

22. The system according to claim 12, wherein said probe is approximately one-half an inch in diameter, said first electrode and said second electrode are each approximately one and one-eighth inches long and are spaced apart from one another by approximately two and five-eighths inches.

23. A system for defibrillating a malfunctioning heart of a subject having lungs, a throat, a trachea, an esophagus and a thorax defined in part by an anterior and a posterior, the system comprising a probe having a distal end and a proximal end, at least a portion of said probe being positionable within the esophagus of the subject; a first electrode carried by said probe; a second electrode carried by said probe and spaced from said first electrode, said first electrode and said second electrode being electrically distinct from one another; a third electrode positionable over a portion of the anterior of the thorax of the subject; a fourth electrode positionable over a portion of the thorax of the subject; a source of electrical defibrillating pulses having a defibrillating output; means for alternatively coupling said defibrillating output between said third electrode and said fourth electrode, and between said third electrode and one of said first and said second electrodes carried by said probe; at least one source of pacing signals having a pacing output; means for coupling said pacing output between one of said first and said second electrodes carried by said probe and said third electrode; sensing means for sensing electrical activity of the heart; and means for coupling and uncoupling said sensing means between said first electrode and said second electrode carried by said probe.

24. The system according to claim 23, wherein said first electrode carried by said probe is carried in vicinity of said distal end.

25. The system according to claim 24, wherein said sensing means for sensing electrical activity of the heart includes display means for displaying an electrocardiogram representing sensed electrical activity of the heart.

26. The system according to claim 24, wherein said sensing means for sensing electrical activity of the heart includes recording means for recording an electrocardiogram representing sensed electrical activity of the heart.

27. The system according to claim 26, wherein said sensing means for sensing electrical activity of the heart further includes display means for displaying an electrocardiogram representing sensed electrical activity of the heart.

28. The system according to claim 23, wherein said sensing means for sensing electrical activity of the heart includes display means for displaying an electrocardiogram representing sensed electrical activity of the heart.

29. The system according to claim 23, wherein said sensing means for sensing electrical activity of the heart includes recording means for recording an electrocardiogram representing sensed electrical activity of the heart.

30. The system according to claim 29, wherein said sensing means for sensing electrical activity of the heart further includes display means for displaying an electrocardiogram representing sensed electrical activity of the heart.

31. The system according to claim 23, wherein said probe is hollow allowing passage of contents from the esophagus and/or the stomach of the subject into said probe.

32. The system according to claim 31, including means for removing the contents from said probe.

33. The system according to claim 23, wherein said probe is approximately one-half an inch in diameter, said first electrode and said second electrode are each approximately one and one-eighth inches long and are spaced apart from one another by approximately two and five-eighths inches.

34. The system according to claim 23, wherein said probe comprises an elongated, flexible electrically nonconductive member having an outer surface and configured so that at least a portion of said member is positionable within the esophagus of the subject; wherein said first electrode is carried by said member on said outer surface in vicinity of said distal end; a second electrode carried by said member on said outer surface and spaced from said first electrode in direction of said proximal end so that when positioned within the esophagus said first electrode and said second electrode are in close proximity to posterior of the heart of the subject, at least one of said first electrode and said second electrode having a large area suitable for passing defibrillating pulses to the heart.

35. The system according to claim 34, wherein said outer surface of said member upon which the first electrode and the second electrode are carried is generally cylindrical, said member has a diameter of approximately one-half an inch, said first electrode is configured as a cylinder and is approximately one and one-eighth inches in length, and said second electrode is spaced from said first electrode by approximately two and five-eighths inches.

36. The system according to claim 35, wherein said second electrode is configured as a cylinder and is approximately one and one-eighth inches in length.

* * * * *